(12) United States Patent
Mann et al.

(10) Patent No.: US 7,229,989 B2
(45) Date of Patent: Jun. 12, 2007

(54) BLUE 3H-NAPHTHO[2,1-B]PYRAN COMPOUNDS AND USE THEREOF IN PHOTOCHROMIC ARTICLES

(75) Inventors: Claudia Mann, Munich (DE); Manfred Melzig, Wessling (DE); Udo Weigand, Munich (DE)

(73) Assignee: Rodenstock GmbH, Munich (DE)

( * ) Notice: Subject to any disclaimer, the term of this patent is extended or adjusted under 35 U.S.C. 154(b) by 44 days.

(21) Appl. No.: 10/945,443

(22) Filed: Sep. 21, 2004

(65) Prior Publication Data

US 2005/0096467 A1 May 5, 2005

Related U.S. Application Data

(63) Continuation of application No. PCT/EP03/02870, filed on Mar. 19, 2003.

(30) Foreign Application Priority Data

Mar. 21, 2002 (DE) ................. 102 12 717
Mar. 22, 2002 (DE) ................. 102 12 991

(51) Int. Cl.
A61K 31/541 (2006.01)
A61K 31/5365 (2006.01)
A61K 31/5383 (2006.01)
C07D 221/18 (2006.01)
C07D 265/34 (2006.01)

(52) U.S. Cl. ................. 514/228.5; 514/232.8; 544/99; 546/43; 546/95

(58) Field of Classification Search ................. 544/60, 544/106, 99; 514/228.5, 232.8; 546/43, 546/95
See application file for complete search history.

(56) References Cited

U.S. PATENT DOCUMENTS 4,818,096 A  4/1989 Trudle et al.
5,990,305 A  11/1999 Melzig et al.

OTHER PUBLICATIONS

Demadrille et al., entitled "1H and 13C NMR chemical shift assignment of some 3H-Naphtho '2,1-b!pyrans", Magnetic Resonance Chemistry, vol. 37, 1999, pp. 328-330.

*Primary Examiner*—Taofiq Solola
(74) *Attorney, Agent, or Firm*—Crowell & Moring LLP

(57) ABSTRACT

Photochromic 3H-naphtho[2,1-b]pyran compounds corresponding to formula I

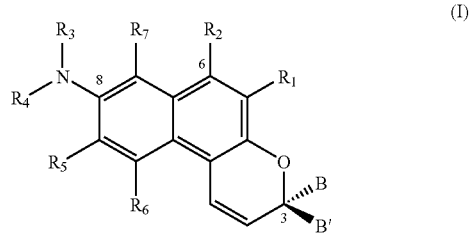

in which the groups $R_1$ to $R_7$ and B' have defined meanings and the use of such photochromic compounds in synthetic resin articles of all types, particularly for ophthalmic purposes. The photochromic 3H-naphtho[2,1-b]pyran derivatives have particularly long-waved absorption maxima in the open form, and when used in photochromic eyeglass lenses, produce essentially blue color tones which have a high darkening capacity.

12 Claims, 1 Drawing Sheet

BLUE 3H-NAPHTHO[2,1-B]PYRAN COMPOUNDS AND USE THEREOF IN PHOTOCHROMIC ARTICLES

CROSS REFERENCE TO RELATED APPLICATIONS

This application is a continuation of international patent application no. PCT/EP03/02870, filed Mar. 19, 2003, designating the United States of America and published in German as WO 03/080595, the entire disclosure of which is incorporated herein by reference. Priority is claimed based on Federal Republic of Germany patent application nos. DE 102 12 717.4, filed Mar. 21, 2002, and DE 102 12 991.6, filed Mar. 22, 2002.

BACKGROUND OF THE INVENTION

The present invention relates to specific photochromic 3H-naphtho[2,1-b]pyran compounds and their use in synthetic resin materials (i.e., plastics) of all types, in particular for ophthalmic purposes. The present invention relates in particular to photochromic compounds derived from 3H-naphtho[2,1-b]pyrans which have especially long wavelength absorption maximums in the open form, so that when used in phototropic glasses, essentially blue tones can be achieved which have a high darkening performance at the same time.

Various classes of dyes are known which undergo a reversible change in color on exposure to light of certain wavelengths. This is due to the fact that these dye molecules are converted to an excited colored state by input of energy in the form of light and leave this state again when the input of energy is interrupted, so that they return to their colorless or at least barely colored normal state. These phototropic dyes include, for example, naphthopyrans, which have already been described in the state of the art with various substituents.

Pyrans, specifically naphthopyrans and larger ring systems derived from them are photochromic compounds which have so far been the object of intense investigations. Although the first patent for these compounds was applied for in the year 1966 (U.S. Pat. No. 3,567,605), it was not until the 1990s that compounds suitable for use in eyeglasses were developed.

The dyes known in the prior art often have an inadequate long wavelength absorption in the excited state as well as in the unexcited state. In combinations with other photochromic dyes, this leads to problems. In addition, there is often too great a sensitivity with regard to the darkening effect, and the brightening takes place too slowly. In addition the dyes available in the state of the art often have an inadequate lifetime. Consequently, such sunglasses do not have an adequate stability. The latter is manifested in a rapid decline in performance and/or severe yellowing.

3H-Naphthopyrans derived from 2-naphthols and similar higher derivatives derived by annellation are a group of photochromic dyes whose longest wavelength absorption maximum of the excited form is mainly in the spectral range from 420 nm to 500 nm and thus they impart a yellow, orange or reddish orange color impression (see U.S. Pat. Nos. 5,869,658 and 6,022,495). For neutral darkening phototropic glasses, however, powerful blue to violet photochromic dyes are needed. Blue to violet photochromic dyes currently available in the state of the art usually come from the class of spiroxazines, fulgides or 2H-naphtho[1,2-b]pyrans. However, spiroxazine dyes are usually at a disadvantage with regard to high temperature performance, whereas fulgide dyes do not have completely satisfactory properties in terms of their lifetime and 2H-naphtho[1,2-b]pyrans do not have fully satisfactory properties with regard to their rate of lightening for use in sunglasses.

Introducing electron shifting substituents on the aryl groups in o-position to the pyran oxygen as described in WO 98/45281, WO 01/12619 and European Patent No. EP 945,451, for example, leads to 3H-naphtho[2,1-b]pyrans that darken to a red or reddish violet shade. WO 01/12619 discloses compounds whose one geminal aryl group has a para-amino-substituted group and whose other aryl group has an alkoxy or thioalkoxy group with a substituent in meta- or para-position; this substitution pattern has a positive influence on the rate of lightening. WO 98/45281 describes red hyperchromic compounds which also have an amine function mainly in position 6 on the 3H-naphtho[2, 1-b]pyran unit. Compounds which do not have pronounced basic amino groups are described in European Patent No. EP 945,451; these compounds have a pinkish to violet color in the excited state and also have an attractive lifetime performance. WO 99/31082 also discloses 3H-naphtho[2,1-b] pyrans with aryl substituents in position 6. The effect of the aryl substitution in position 6 on the longest wavelength absorption maximum of the excited and unexcited forms is very minor with these compounds, however.

Corresponding substitution in the 8-position of the 3H-naphtho[2,1-b]pyran unit produces a bathochromic shift of the longest wavelength absorption maximum, especially by introduction of alkoxy groups as described in U.S. Pat. No. 5,238,981. In addition, compounds with dialkylamino groups in the 8-position have also been disclosed. The use of nitrogen heterocycles as substituents in position 8 of the 3H-naphtho[2,1-b]pyran unit is mentioned in U.S. Pat. No. 5,990,305, so that an improved lifetime is achieved in contrast with open-chain amino groups. This is also achieved with substituents containing so-called HALS (hindered amine light stabilizer) structure units. Finally, published German Patent application no. DE 102 00 040 describes blue to violet 3H-naphtho[2,1-b]-pyrans which have substituents with amino groups in positions 3 and 8.

SUMMARY OF THE INVENTION

It is an object of the present invention to provide improved photochromic dyes, particularly with a blue color.

Another object of the invention is to provide photochromic compounds which have improved properties in comparison with compounds described in the prior art.

A further object of the invention is to provide photochromic compounds characterized by an improved combination of long wavelength absorption in the excited state and high darkening performance.

It is also an object of the invention to provide photochromic dyes which simultaneously exhibit good kinetic properties and a long service life, i.e., they have rapid lightening rate and perform favorably in the service life test in comparison with comparable compounds from the prior art.

These and other objects have been achieved in accordance with the present invention by providing a photochromic 3H-naphtho[2,1-b]pyran compound corresponding to formula (I):

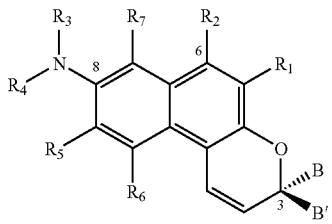

wherein

R$_1$, R$_5$, R$_6$ and R$_7$ are independently selected from hydrogen or a substituent selected from the group α consisting of fluoro, chloro, bromo, hydroxy, silyloxy, amino, linear or branched (C$_1$–C$_6$) alkyl, (C$_3$–C$_7$) cycloalkyl, linear or branched (C$_1$–C$_6$) alkoxy, morpholinyl, thiomorpholinyl, piperidinyl, piperazinyl, pyrrolidinyl, imidazolinyl, pyrazolidinyl, 1,2,3,4-tetrahydroquinolinyl, 1,2,3,4-tetrahydroisoquinolinyl, perhydroazepinyl, 4-methylperhydro-1,4-diazepinyl, perhydroazocinyl, phenyl, phenoxy, benzyl, benzyloxy, naphthyl, naphthoxy, phenanthryl, and pyridyl, each substituted with zero, one, two or three substituents, independently selected from the group β consisting of linear or branched (C$_1$–C$_6$) alkyl, (C$_3$–C$_7$) cycloalkyl, linear or branched (C$_1$–C$_6$) alkoxy, hydroxy, tert-butyldiphenyl-silyloxy, amino, di(C$_1$–C$_6$)alkylamino, nitro, cyano, benzyl, 4-methoxy-benzyl, 4-nitrobenzyl, phenyl, 4-methoxyphenyl, 4-dimethylaminophenyl, pyridyl and pyrimidinyl;

R$_2$ is selected from the group α, or is selected from the group consisting of quinolinyl, isoquinolinyl, thienyl, benzothienyl, dibenzothienyl, furanyl, benzofuranyl, dibenzofuranyl, carbazolyl, phenothiazinyl, phenoxazinyl, oxazolyl, benzoxazolyl, oxadiazolyl, thiazolyl, benzothiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminomethyl, N-hydroxyiminomethyl, methyleneamino, cyanamino, cyanomethyl, dicyanomethyl, carboxy, carboxymethyl, (C$_1$–C$_6$) acyloxy, (C$_1$–C$_6$) alkoxycarbonyl, (C$_1$–C$_6$) alkoxycarbonylmethyl, phenoxycarbonyl, benzyloxycarbonyl, nitro, diazophenyl, aminocarbonyl, ethenyl, 4-ethenylphenyl, ethynyl, and 4-ethynylphenyl; or represents a cationic structure formed from a N-(C$_1$–C$_6$)-alkylpyridinio, 1-pyridinio, N-(C$_1$–C$_6$)-alkylquinolinio, 1-quinolinio, N—(C$_1$–C$_6$) alkylisoquinolinio, 2-isoquinolinio, iminiomethyl or 1-iminioaminomethyl group paired with an anion selected from the group consisting of chloride, bromide, sulfate, hydrogen sulfate, tetrafluoroborate, hexafluorophosphate, mesylate, tosylate and triflate;

wherein R2 may optionally be substituted with one, two, three or four substituents selected from the group β; or R$_2$ together with R$_7$ may form a U—(V)$_p$—W group, where p is 0, 1 or 2 and U, V and W are independently selected from the group consisting of carbonyl, oxygen, sulfur, N—CH$_3$, N—C$_6$H$_5$, CH$_2$, C(CH$_3$)$_2$ and C(C$_6$H$_5$)$_2$; or R$_2$ is a Y-naphthyl group, where Y is a linker between the naphthyl group and the naphthopyran unit, said linker Y being selected from the group consisting of a single bond, CH$_2$, ethanediyl, ethenediyl, ethynediyl, iminomethyl, phenylene, biphenyldiyl, ferrocenediyl, pyridinediyl, pyrimidinediyl, pyrazinediyl and (bipyrimidinyl)diyl, wherein the naphthyl radical optionally may substituted by one, two, three or four substituents selected from the group α or by an —NR$_3$R$_4$ group as defined hereinbelow, wherein one of the naphthyl substituents together with the R$_4$ radical of the —NR$_3$R$_4$ group bound to the naphthyl radical may form an —R$_4$N—(CH$_2$)$_k$—X group, where k=1 or 2, bound to the aromatic ring of the naphthyl radical, in which R$_4$ is then selected from the group consisting of hydrogen, linear or branched C$_1$–C$_6$ alkyl and phenyl, and X denotes oxygen, sulfur, CH$_2$, C(CH$_3$)$_2$, C(C$_6$H$_5$)$_2$, NCH$_3$ or NPh, and wherein a benzene ring may be annellated to the —R$_4$N—(CH$_2$)$_k$—X group; or wherein two of the naphthyl substituents may form a pyran ring annellated at the naphthyl radical of the Y-naphthyl group, which in turn may be substituted with B and B' so that a second photochromic naphthopyran system bound by the linker Y is obtained;

R$_3$ and R$_4$ are independently selected from the group consisting of hydrogen, linear or branched (C$_1$–C$_6$) alkyl, (C$_3$–C$_7$) cycloalkyl, (C$_1$–C$_6$) alkoxy, phenyl and benzyl, wherein if R3 or R4 is phenyl or benzyl, it may be substituted by one or more substituents selected from the group β, or R$_3$ and R$_4$ together with the nitrogen atom to which they are bound may form an azaadamantyl group or a 3- to 10-membered nitrogen heterocycle which may be unsubstituted or substituted with linear or branched (C$_1$–C$_6$) alkyl; said nitrogen heterocycle optionally containing one or more heteroatoms selected from the group consisting of O, S and NR$^8$, where R$^8$ is hydrogen or is selected from the group β, and wherein the nitrogen heterocycle optionally may be annellated with one or two benzene rings; or R$_4$ and R$_5$, or R$_3$ and R$_7$, or both, together with the nitrogen atom form an —R$_4$N—(CH$_2$)$_k$—X— or —R$_3$N—(CH$_2$)$_k$—X— unit bound to the benzene ring of the naphthopyran structure, where k=1 or 2, and X is O, S, CH$_2$, C(CH$_3$)$_2$, C(C$_6$H$_5$)$_2$, N(CH$_3$) or N(C$_6$H$_5$), and at least one of R$_4$ and R$_3$ then is methyl or phenyl, and wherein a benzene ring optionally may be annellated to the —R$_4$N—(CH$_2$)$_k$—X— unit or —R$_3$N—(CH$_2$)$_k$—X— unit, or NR$_3$R$_4$, R$_5$ and R$_7$ together with the benzene ring of the naphthopyran structure to which they are bound form a julolidinyl unit, B and B' independently of one another are selected from unsubstituted, monosubstituted or disubstituted phenyl, ethynyl, ethenyl, naphthyl, furanyl, benzofuranyl, thienyl, benzothienyl or julolidinyl, whereby the substituents are selected from the α group as well as ethenyl, 4-ethenylphenyl, ethynyl or 4-ethynylphenyl, where the substituents from the α group as well as the substituents listed above, again independently of one another, may each have two or three substituents from the β group or whereby two directly vicinal substituents may form an X—(CH$_2$)$_q$-Z group where q=1, 2 or 3 and X and Z independently of one another denote oxygen, sulfur, NCH$_3$, NPh, CH$_2$, C(CH$_3$)$_2$ or C(C$_6$H$_5$)$_2$, or B and B' together form an unsubstituted, monosubstituted or disubstituted 9-spirofluorene group, optionally substituted with one or more substituents selected from the group β, or B and B' together form a saturated hydrocarbon which is C$_3$–C$_{12}$ spiromonocyclic, C$_7$–C$_{12}$ spirobicyclic or C$_7$–C$_{12}$ spirotricyclic.

In particular photochromic 3H-naphtho[2,1-b]pyran derivatives with general formula (I) are made available:

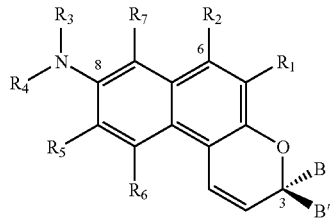

in which
the $R_1$, $R_5$, $R_6$ and $R_7$ groups, independently of one another, represent hydrogen or a substituent selected from the α group, which consists of fluoro, chloro, bromo, hydroxy, silyloxy, amino, a linear or branched ($C_1$–$C_6$) alkyl radical, a ($C_3$–$C_7$) cycloalkyl radical, a linear or branched ($C_1$–$C_6$) alkoxy radical, morpholinyl, thiomorpholinyl, piperidinyl, piperazinyl, pyrrolidinyl, imidazolinyl, pyrazolidinyl, 1,2,3,4-tetrahydroquinolinyl, 1,2,3,4-tetrahydroisoquinolinyl, perhydroazepinyl, 4-methylperhydro-1,4-diazepinyl, perhydroazocinyl, phenyl, phenoxy, benzyl, benzyloxy, naphthyl, naphthoxy, phenanthryl or pyridyl, each optionally substituted with one, two or three substituents, selected independently of one another from the β group which consists of a linear or branched ($C_1$–$C_6$) alkyl radical, a ($C_3$–$C_7$) cycloalkyl radical, a linear or branched ($C_1$–$C_6$) alkoxy radical, hydroxy, tert-butyldiphenylsilyloxy, amino, di($C_1$–$C_6$)alkylamino, nitro, cyano, benzyl, 4-methoxybenzyl, 4-nitrobenzyl, phenyl, 4-methoxyphenyl, 4-dimethylaminophenyl, pyridyl and pyrimidinyl;

$R_2$ is selected from a substituent of the α group or quinolinyl, isoquinolinyl, thienyl, benzothienyl, dibenzothienyl, furanyl, benzofuranyl, dibenzofuranyl, carbazolyl, phenothiazinyl, phenoxazinyl, oxazolyl, benzoxazolyl, oxadiazolyl, thiazolyl, benzothiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminomethyl, N-hydroxyiminomethyl, methyleneamino, cyanamino, cyanomethyl, dicyanomethyl, carboxy, carboxymethyl, ($C_1$–$C_6$) acyloxy, ($C_1$–$C_6$) alkoxycarbonyl, ($C_1$–$C_6$) alkoxycarbonylmethyl, phenoxycarbonyl, benzyloxycarbonyl, nitro, diazophenyl, aminocarbonyl, ethyl, 4-ethenylphenyl, ethynyl or 4-ethynylphenyl or from N-($C_1$–$C_6$)-alkylpyridinio, 1-pyridinio, N—($C_1$–$C_6$)-alkylquinolinio, 1-quinolinio, N—($C_1$–$C_6$)-alkylisoquinolinio, 2-isoquinolinio, iminiomethyl [sic] or 1-iminioaminomethyl [sic], forming a cationic structure, whereby the corresponding counterion is selected from chloride, bromide, sulfate, hydrogen sulfate, tetrafluoroborate, hexafluorophosphate, mesylate, tosylate or triflate, whereby the substituents above may each have one, two, three or four substituents from the β group, or $R_2$ together with $R_7$ may form a U—(V)$_p$—W group, where p is 0, 1 or 2 and U, V and W, independently of one another, may represent carbonyl, oxygen, sulfur, N—CH$_3$, N—C$_6$H$_5$, CH$_2$ C(CH$_3$)$_2$ or C(C$_6$H$_5$)$_2$;

or $R_2$ may represent a Y-naphthyl group, where Y is a linker between the naphthyl group and the naphthopyran unit, selected from a direct single bond or CH$_2$, ethanediyl, ethenediyl, ethynediyl, iminomethyl, phenylene, biphenyldiyl, ferrocenediyl, pyridinediyl, pyrimidinediyl, pyrazinediyl or (bipyrimidinyl)diyl and wherein the naphthyl radical may have one, two, three or four substituents, selected from the α group or an —NR$_3$R$_4$ group as defined below, where one of the naphthyl substituents together with the R$_4$ radical of the —NR$_3$R$_4$ group attached to the naphthyl radical may form an —R$_4$N—(CH$_2$)$_k$—X group, where k=1 or 2, attached to the aromatic ring of the naphthyl radical, where the R$_4$ radical is then hydrogen, a linear or branched $C_1$–$C_6$ alkyl radical or phenyl and X is oxygen, sulfur, CH$_2$, C(CH$_3$)$_2$, C(C$_6$H$_5$)$_2$, NCH$_3$ or NPh, and where a benzene may again be annellated onto this —R$_4$N—(CH$_2$)$_k$—X group; or where two of the naphthyl substituents may form a pyran ring annellated at the naphthyl radical of the Y-naphthyl group, and this ring may in turn be substituted with B and B' as defined below so that a second photochromic naphthopyran system bound by the linker Y is obtained;

$R_3$ and $R_4$ are independently selected from hydrogen, a linear or branched ($C_1$–$C_6$) alkyl radical, a ($C_3$–$C_7$) cycloalkyl radical, a ($C_1$–$C_6$) alkoxy radical, phenyl or benzyl, whereby phenyl or benzyl may have one or more substituents from the β group, or $R_3$ and $R_4$ together with the nitrogen atom to which they are bound may form an azaadamantyl group or a 3- to 10-membered nitrogen heterocycle which may be unsubstituted or substituted with a linear or branched ($C_1$–$C_6$) alkyl radical, whereby the nitrogen heterocycle may contain one or more heteroatoms from the group O, S or NR$^8$, wherein R$^8$ is selected from hydrogen or the β group, and wherein the nitrogen heterocycle may be annellated with one or two benzene rings, or $R_4$ and $R_5$ and/or $R_3$ and $R_7$ radicals together, including the nitrogen atoms to which they are bound, may form a —R$_4$N—(CH$_2$)$_k$—X— or —R$_3$N—(CH$_2$)$_k$—X— unit, where k=1 or 2, which is bound to the benzene ring of the naphthopyran structure, where X is selected from O, S, CH$_2$, C(CH$_3$)$_2$, C(C$_6$H$_5$)$_2$, N(CH$_3$) or N(C$_6$H$_5$) and R$_4$ and/or R$_3$ is then selected from methyl or phenyl, again with a benzene ring optionally being annellated on this —R$_4$N—(CH$_2$)$_k$—X— or —R$_3$N—(CH$_2$)$_k$—X— unit, or NR$_3$R$_4$, R$_5$ and R$_7$ together with the benzene ring of the naphthopyran structure to which they are attached may form a juloidinyl unit, and B and B' are independently are selected from unsubstituted, monosubstituted or disubstituted phenyl, ethynyl, ethenyl, naphthyl, furanyl, benzofuranyl, thienyl, benzothienyl or julolidinyl, where the substituents are selected from the α group plus ethenyl, 4-ethenylphenyl, ethynyl or 4-ethynylphenyl, wherein the substituents from the α group as well as the preceding substituents may in turn each have, insofar as possible, two or three substituents independently selected from the β group, or wherein two directly vicinal substituents may form an X—(CH$_2$)$_q$-Z group where q=1, 2 or 3, and X and Z independently represent oxygen, sulfur, NCH$_3$, NPh, CH$_2$, C(CH$_3$)$_2$ or C(C$_6$H$_5$)$_2$, or B and B' together may denote an unsubstituted, monosubstituted or disubstituted 9-spirofluorene wherein the fluorene substituents are selected from the β group, or B and B' together may form a saturated hydrocarbon which is $C_3$–$C_{12}$ spiromonocyclic, $C_7$–$C_{12}$ spirobicyclic or $C_7$–$C_{12}$ spirotricyclic.

By introducing a substituent having an amino group in position 8 on the naphthopyran basic structure and at the same time a specific substituent in position 6, especially a substituent which enlarges the π-electron system of the molecule, the photochromic properties of 3H-naphtho[2,1-b]pyrans, in particular their darkening performance, can be increased significantly. In comparison with corresponding prior art compounds, 3H-naphtho[2,1-b]pyrans are provided which, in the excited form, absorb at a much longer wavelength and at the same time have a high darkening performance. This makes it possible to produce blue photochromic dyes in only a few reaction steps. In addition, the photochromic 3H-naphtho[2,1-b]pyrans of the invention combine a good service life and rapid lightening rates with an uncommonly good darkening performance.

DETAILED DESCRIPTION OF PREFERRED EMBODIMENTS

Figure 1:
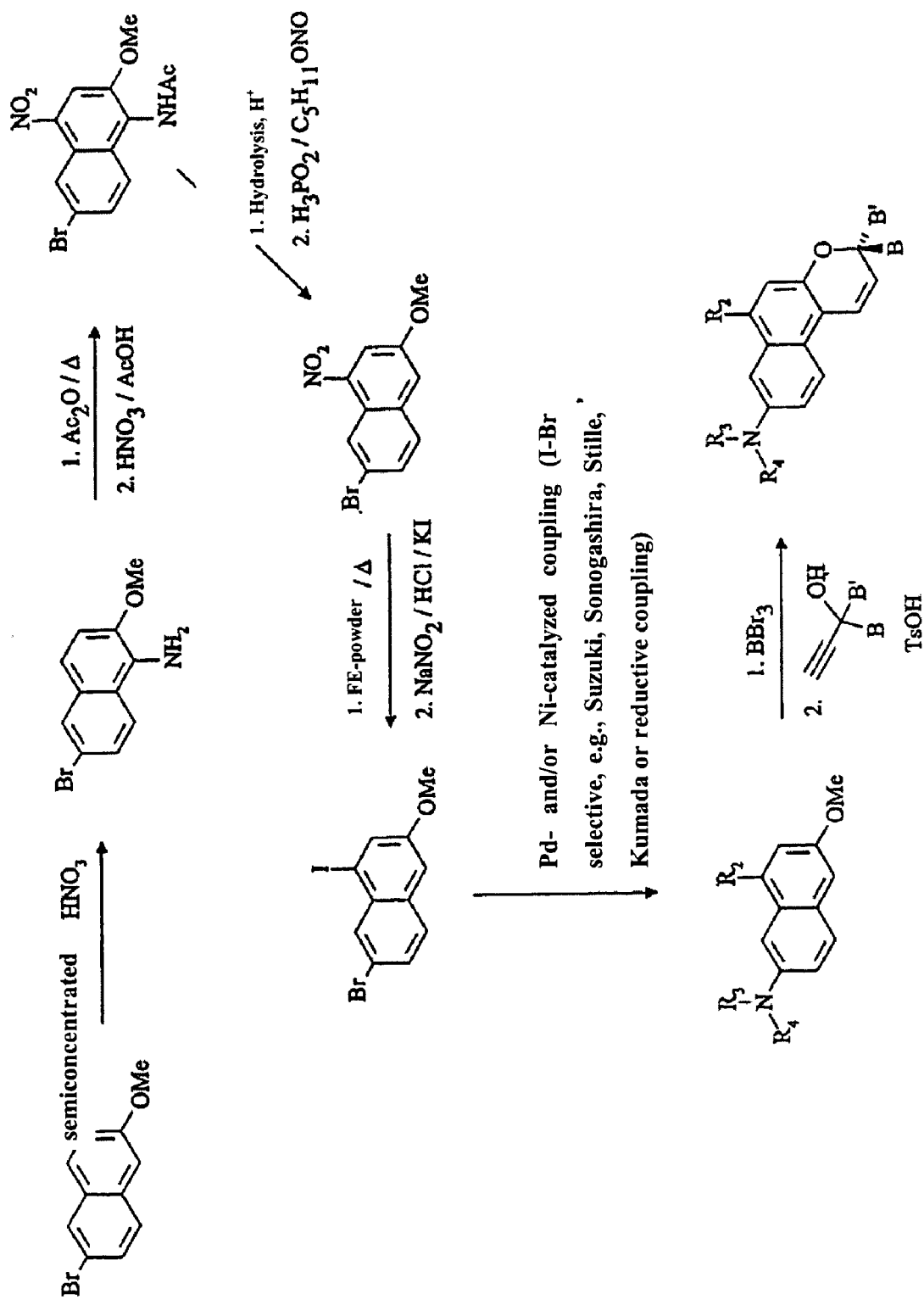
FIG. 1 shows as an example a synthesis pathway for production of illustrative photochromic compounds according to the inventioin.

In a preferred embodiment of the present invention, the $R_2$ radical is selected from phenyl, naphthyl, pyridyl, oxazolyl, oxadiazolyl, thiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-imino-aminomethyl, 1-(aminomethylene)-2-iminoethyl, N-hydroxyimino-methyl, methyleneamino, cyanoamino, dicyanomethyl, carboxymethyl, $(C_1-C_6)$-alkoxycarbonyl, nitro, ethenyl, 4-ethenylphenyl, ethynyl or 4-ethynylphenyl, each of which may have, insofar as possible, one, two, three or four substituents from the β group, or the $R_2$ radical represents a Y-naphthyl group, where Y is a linker between the naphthyl group and the naphthopyran, selected from a single bond or $CH_2$, ethanediyl, ethenediyl, ethynediyl, iminomethyl, phenylene, biphenyldiyl, ferrocenediyl, pyridinediyl, pyrimidinediyl, pyrazinediyl or (bipyrimidinyl)diyl and where the naphthyl radical may have one, two, three or four substituents, selected from the α group or an —$NR_3R_4$ group, as already defined above whereby one of the naphthyl substituents together with the $R_4$ radical of the —$NR_3R_4$ group attached to the naphthyl radical may form an —$R_4N$—$(CH_2)_k$—X group, where k=1 or 2 attached to the aromatic ring of the naphthyl radical, where the $R_4$ radical then denotes hydrogen, a linear or branched $C_1$–$C_6$ alkyl radical or phenyl and X denotes oxygen, sulfur, $CH_2$, $C(CH_3)_2$, $C(C_6H_5)_2$, $NCH_3$ or NPh, and where a benzene ring may again be annellated at this —$R_4N$—$(CH_2)_k$—X group; or where two of the naphthyl substituents form a pyran ring annellated at the naphthyl radical of the Y-naphthyl group, this pyran ring in turn being substituted optionally with B and B' as defined above, yielding a second photochromic naphthopyran system bound by the linker Y, i.e., a 3H-naphtho[2,1-b]pyran characterized by formula (I) given above may be bound by the linker Y to another 3H-naphtho[2,1-b]pyran, which may be the same or different.

In an especially preferred embodiment, $R_2$ represents phenyl, 4-methoxyphenyl, 4-nitrophenyl, 4-(2-pyrimidinyl) phenyl, 2-pyridyl, 3-pyridyl, 4-pyridyl, 2-pyrimidinyl, 2-pyrazinyl, 5-methyl-2-oxadiazolyl, 2,4-dimethyl-1-pyrazolyl, 4,5-dimethyl-2-imidazolyl, 1-hex-1-inyl, phenylethynyl or 4-pyridylethynyl or $R_2$ is a linker between the substituents in position 6 of the two 3H-naphtho[2,1-b]pyrans defined as described above, whereby the linker is selected from a direct bond, ethenediyl, ethynediyl, 1,4-phenylene or 5,5'-bipyrimidinyl-2,2'-diyl.

In another preferred embodiment of the present invention, $R_3$ and $R_4$ according to the foregoing formula (I) are selected from an unsubstituted, monosubstituted or disubstituted phenyl, phenoxy, benzyl, benzyloxy, naphthyl or naphthoxy radical or together with the nitrogen atom they form a three- to ten-membered nitrogen heterocycle, especially a morpholine group, a thiomorpholine group, a piperidine group, an azacycloheptane group, an azacyclooctane group, a 1,4-diaza-1-methylcycloheptane group, a piperazine group, a (N'—($C_1$–$C_6$-alkyl)piperazine group, a pyrrolidine group, an imidazolidine group, a pyrazolidine group, an aziridine group, a azetidine group, an indoline group, a carbazole group, a phenothiazine group, a phenazine group, a phenoxazine group, a tetrahydroquinoline group or a tetrahydroisoquinoline group. Even more preferably, the $NR_3R_4$ group in the foregoing formula (I) denotes in its entirety diphenylamino, dianisylamino, morpholinyl, thiomorpholinyl, 3,5-dimethylthiomorpholinyl, piperidinyl, azacycloheptyl, azacyclooctyl, 1,4-diaza-1-methylcycloheptyl, piperazinyl, pyrrolidinyl or 1,2,3,4-tetrahydroisoquinolinyl.

If the $NR_3R_4$, $R_5$ and $R_7$ radicals together with the benzene ring of the naphthopyran structure to which they are attached form a julolidinyl unit, this yields the following structural unit:

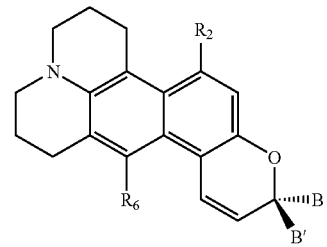

Julolidinyl Substitution

If the $R_3$ and $R_7$ and/or $R_4$ and $R_5$ radicals together form a —$R_3N$—$(CH_2)_k$—X— and/or —$R_4N$—$(CH_2)_k$—X— unit, as defined above, attached to the benzene ring of the naphthopyran structure and including the nitrogen atom, then the following structural units are preferred:

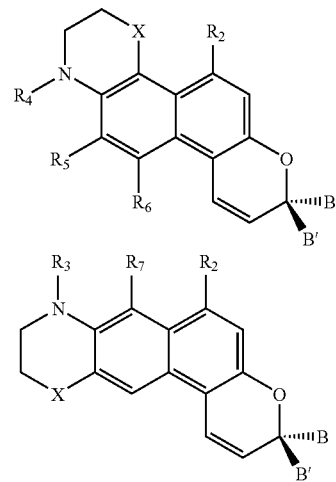

X in the preceding structural units is preferably selected from O, $CH_2$ and $N(CH_3)$.

In another preferred embodiment of the present invention, at least one of the B and B' radicals is a phenyl group which is substituted in para-position with an —NR₃R₄ group as defined above. The R₃ and R₄ radicals together with the nitrogen atom on this NR₃R₄ group may also form an azaadamantyl group. Alternatively, they also may form a three- to ten-membered nitrogen heterocycle having the definition given above, in particular a morpholine group, a thiomorpholine group, a piperidine group, a azacycloheptane group, a azacyclooctane group, a 1,4-diaza-1-methyl-cycloheptane group, a piperazine group, an N—(N'—(C₁–C₆-alkyl)piperazine group or a pyrrolidine group, or the phenyl radical substituted in para-position with an —NR₃R₄ group as a whole may represent an N-methyl-1,2,3,4-tetrahydroquinolinyl group bound in position 6, yielding the following structural unit:

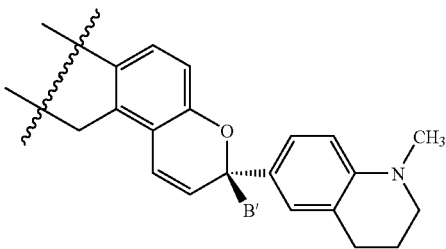

In another preferred embodiment at least one of the B and/or B' radicals is a 4-dimethylaminophenyl group.

If one of the B and B' radicals represents a julolidinyl radical bound to the pyran ring at position 3, this yields the following structural unit:

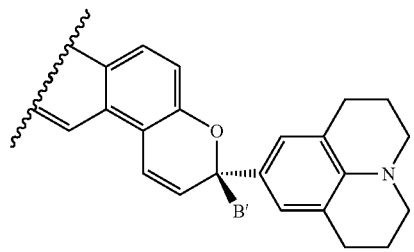

The absorption maximums having the longest wavelength of the open (colored) form of two illustrative photochromic 3H-naphtho[2,1-b]pyran compounds according to the present invention are listed as examples in the following table.

to the invention in which R₂ is phenyl and/or with compound (3) according to the invention in which R₂ is phenylethynyl demonstrates that introducing a substituent in position 6 produces 3H-naphtho[2,1-b]pyran compounds which absorb at a much longer wavelength in the excited form.

The compounds according to the invention may be used in synthetic resins (i.e., plastics) and/or synthetic resin articles of any type and form for a variety of applications in which the photochromic property is important. A dye according to the present invention or a mixture of such dyes may be used. For example, the photochromic 3H-naphtho[2,1-b]pyran dyes according to the invention may be used in lenses, in particular in ophthalmic lenses, lenses for eyeglasses of all types such as ski goggles, sunglasses, motorcycle goggles, visors of safety helmets and the like. Furthermore, the photochromic dyes according to the invention may also be used as sun protection in vehicles and residences in the form of windows, sun visors, covers, roofs or the like.

To produce such photochromic articles, the photochromic 3H-naphtho[2,1-b]pyran dyes according to the invention may be applied to or embedded in a polymer material such an organic plastic material by various methods known in the art, for example as disclosed in WO 99/15518.

A distinction is made between so-called bulk dyeing processes and surface dyeing processes. A bulk dyeing process includes, for example, dissolving or dispersing the photochromic compound or compounds according to the present invention in a plastic material, e.g., by adding the photochromic compound(s) to a monomer material before polymerization. Another possibility for producing a photochromic article is by having the photochromic compound(s) penetrate into the synthetic resin material(s) by immersing the synthetic resin material in a hot solution of the photochromic dye(s) according to the present invention or, for example, by a thermal transfer method. The photochromic compound(s) may also be provided, for example, in the form of a separate layer between adjacent layers of the synthetic resin material, e.g., as part of a polymer film. Furthermore, it is also possible to apply the photochromic compound(s) as part of a coating on the surface of the synthetic resin material. The term "penetrate" should be understood here to mean the migration of the photochromic compound(s) into the synthetic resin material, e.g., through solvent-supported transfer of the photochromic compound(s) into a polymer matrix, vapor phase transfer or other such surface diffusion processes. Photochromic articles such as eyeglasses may also be manufactured not only by the usual bulk dyeing, but likewise also by surface dyeing, in which case a surprisingly

| Compound | R₂ | NR₃R₄ | B | B' | R₁ = R₅ = R₆ = R₇ | λmax |
|---|---|---|---|---|---|---|
| (1) | H | N-Piperidinyl | 4-Dimethylaminophenyl | Phenyl | H | 570 nm |
| (2) | Phenyl | N-Piperidinyl | 4-Dimethylaminophenyl | Phenyl | H | 585 nm |
| (3) | Phenylethynyl | N-Piperidinyl | 4-Dimethylaminophenyl | Phenyl | H | 615 nm |

λmax: Absorption maximum at the longest wavelength of the open (colored) form (measured in methacrylate polymer).

Compound (1) is a reference compound from the prior art (German Patent DE 102 00 40) in which R₂ is hydrogen. A comparison of compound (1) with compound (2) according lower migration tendency can be achieved with the latter variant. This is an advantage especially in the subsequent upgrading steps because separation of layers and similar defects are drastically reduced, e.g., due to the lower back diffusion in vacuo in the case of an antireflective coating.

All in all, based on the photochromic 3H-naphtho[2,1-b]pyran dyes according to the invention, any desired coloration, i.e, dyestuff, which is compatible both from a chemical standpoint and coloristically, can be applied to or embedded in a synthetic resin to satisfy aesthetic requirements as well as medical or fashion demands. Of course, the specific dye combinations selected may vary depending on the intended effects to be achieved and requirements to be met.

The photochromic 3H-naphtho[2,1-b]pyran dyes according to the invention corresponding to formula (I) can be produced, for example, according to the reaction scheme given in FIG. 1.

The key step in synthesis of the compounds according to this invention is, starting from 6-bromo-4-iodo-2-methoxynaphthaline, the palladium- or nickel-catalyzed coupling with a marked I/Br selectivity. Through a suitable choice of reaction conditions with which those skilled in the art are familiar, it is possible to replace only the iodine group with the $R_2$ radical, e.g., by coupling of the Suzuki type, the Sonogashira type, the Stille type or the Kumada type or a reductive dimerization reaction. Then the optionally substituted amino group is introduced into the naphthalene system by palladium-catalyzed amination. After ether cleavage, the resulting 2-naphthol derivatives are reacted with appropriately substituted 2-propin-1-ol derivatives to yield the compounds according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A photochromic 3H-naphtho[2,1-b]pyran compound corresponding to formula (I):

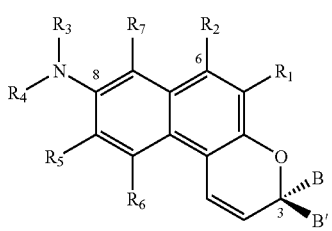

(I)

wherein
$R_1$, $R_5$, $R_6$ and $R_7$ are independently selected from hydrogen or a substituent selected from the group α consisting of fluoro, chloro, bromo, hydroxy, silyloxy, amino, linear or branched ($C_1$–$C_6$) alkyl, ($C_3$–$C_7$) cycloalkyl, linear or branched ($C_1$–$C_6$) alkoxy, morpholinyl, thiomorpholinyl, piperidinyl, piperazinyl, pyrrolidinyl, imidazolinyl, pyrazolidinyl, 1,2,3,4-tetrahydroquinolinyl, 1,2,3,4-tetrahydroisoquinolinyl, perhydroazepinyl, 4-methylperhydro-1,4-diazepinyl, perhydroazocinyl, phenyl, phenoxy, benzyl, benzyloxy, naphthyl, naphthoxy, phenanthryl, and pyridyl, each substituted with zero, one, two or three substituents, independently selected from the group β consisting of linear or branched ($C_1$–$C_6$) alkyl, ($C_3$–$C_7$) cycloalkyl, linear or branched ($C_1$–$C_6$) alkoxy, hydroxy, tert-butyldiphenyl-silyloxy, amino, di($C_1$–$C_6$)alkylamino, nitro, cyano, benzyl, 4-methoxybenzyl, 4-nitrobenzyl, phenyl, 4-methoxyphenyl, 4-dimethylaminophenyl, pyridyl and pyrimidinyl;

$R_2$ is selected from the group α, or is selected from the group consisting of quinolinyl, isoquinolinyl, thienyl, benzothienyl, dibenzothienyl, furanyl, benzofuranyl, dibenzofuranyl, carbazolyl, phenothiazinyl, phenoxazinyl, oxazolyl, benzoxazolyl, oxadiazolyl, thiazolyl, benzothiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminomethyl, N-hydroxyiminomethyl, methyleneamino, cyanamino, cyanomethyl, dicyanomethyl, carboxy, carboxymethyl, (C–$C_6$) acyloxy, ($C_1$–$C_6$) alkoxycarbonyl, ($C_1$–$C_6$) alkoxycarbonylmethyl, phenoxycarbonyl, benzyloxycarbonyl, nitro, diazophenyl, aminocarbonyl, ethenyl, 4-ethenylphenyl, ethynyl, and 4-ethynylphenyl; or represents a cationic structure formed from a N—($C_1$–$C_6$)-alkylpyridinio, 1-pyridinio, N—($C_1$–$C_6$)-alkylquinolinio, 1-quinolinio, N—($C_1$–$C_6$) alkylisoquinolinio, 2-isoquinolinio, iminiomethyl or 1-iminioaminomethyl group paired with an anion selected from the group consisting of chloride, bromide, sulfate, hydrogen sulfate, tetrafluoroborate, hexafluorophosphate, mesylate, tosylate and triflate;

wherein R2 may optionally be substituted with one, two, three or four substituents selected from the group β; or R2 is a Y-naphthyl group, where Y is a linker between the naphthyl group and the naphthopyran unit, said linker Y being selected from the group consisting of a single bond, $CH_2$, ethanediyl, ethenediyl, ethynediyl, iminomethyl, phenylene, biphenyldiyl, ferrocenediyl, pyridinediyl, pyrimidinediyl, pyrazinediyl and (bipyrimidinyl)diyl, wherein the naphthyl radical optionally may substituted by one, two, three or four substituents selected from the group α or by an —$NRaR_4R_4$ group; and wherein two of the naphthyl substituents may form a pyran ring annellated at the naphthyl radical of the Y-naphthyl group, which in turn may be substituted with B and B' so that a second photochromic naphthopyran system bound by the linker Y is obtained;

$R_3$ and $R_4$ are independently selected from the group consisting of hydrogen, linear or branched ($C_1$–$C_6$) alkyl, ($C_3$–$C_7$) cycloalkyl, ($C_1$–$C_6$) alkoxy, phenyl and benzyl, wherein if R3 or R4 is phenyl or benzyl, it may be substituted by one or more substituents selected from the group β, or $R_3$ and $R_4$ together with the nitrogen atom to which they are bound may form an azaadamantyl group or a 3- to 10-membered nitrogen heterocycle which may be unsubstituted or substituted with linear or branched ($C_1$–$C_6$) alkyl;

said nitrogen heterocycle optionally containing one or more heteroatoms selected from the group consisting of O, S and $NR^8$, where $R^8$ is hydrogen or is selected from the group β, and wherein the nitrogen heterocycle optionally may be annellated with one or two benzene rings; and B and B' independently of one another are selected from unsubstituted, monosubstituted or disubstituted phenyl, ethynyl, ethenyl, naphthyl, furanyl, benzofuranyl, thienyl, benzothienyl or julolidinyl, whereby the substituents are selected from the a group as well as ethenyl, 4-ethenylphenyl, ethynyl or 4-ethynylphenyl, where the substituents from the α group as well as the substituents listed above, again independently of one another, may each have two or three substituents from the β group or whereby two directly vicinal substituents may form an X—$(CH_2)_q$-Z group where q=1, 2 or 3 and X and Z independently of one another denote oxygen, sulfur, $NCH_3$, NPh, $CH_2,C(CH_3)_2$ or $C(C_6H_5)_2$.

2. A compound according to claim 1, wherein $R_2$ is selected from the group consisting of phenyl, naphthyl, pyridyl, oxazolyl, oxadiazolyl, thiazolyl, thiadiazolyl, imidazolyl, pyrazolyl, triazolyl, tetrazolyl, pyrimidinyl, pyrazinyl, acetyl, benzoyl, cyano, formyl, iminomethyl, 1-iminoaminomethyl, 1-(aminomethylene)-2-iminoethyl, N-hydroxyiminomethyl, methyleneamino, cyanoamino, dicyanomethyl, carboxymethyl, ($C_1$–$C_6$)-alkoxycarbonyl, nitro, ethenyl, 4-ethenylphenyl, ethynyl and 4-ethynylphenyl, each of which may have up to four substituents from the β group.

3. A compound according to claim 1, wherein $R_2$ represents a Y-naphthyl group, wherein Y is a linker between the naphthyl group and the naphthopyran unit, said linker being selected from the group consisting of a single bond, $CH_2$, ethanediyl, ethenediyl, ethynediyl, iminomethyl, phenylene, biphenyldiyl, ferrocenediyl, pyridinediyl, pyrimidinediyl, pyrazinediyl and (bipyrimidinyl)diyl; and wherein the naphthyl radical may have one, two, three or four substituents, selected from the a group or an —$NR_3R_4$ group;

wherein two naphthyl substituents may form a pyran ring annellated to the naphthyl radical of the Y-naphthyl group, which may in turn have B and B' substituents so that a second photochromic naphthopyran system is obtained, bound by the linker Y.

4. A compound according to claim 1, wherein $R_2$ represents phenyl, 4-methoxyphenyl, 4-nitrophenyl, 4-(2-pyrimidinyl)phenyl, 2-pyridyl, 3-pyridyl, 4-pyridyl, 2-pyrimidinyl, 2-pyrazinyl, 5-methyl-2-oxadiazolyl, 2,4-dimethyl-1-pyrazolyl, 4, 5-dimethyl-2-imidazolyl, 1-hex-1-inyl, phenyl ethynyl or 4-pyridylethynyl.

5. A compound according to claim 1, wherein $R_2$ represents a linker between the 6-substituents of two 3H-naphtho[2,1-b]pyran structures, said linker being selected from the group consisting of a direct bond, ethenediyl, ethynediyl, 1,4-phenylene, and 5,5'-bipyrimidinyl-2,2'-diyl.

6. A compound according to claim 1, wherein $R_3$ and $R_4$ are independently selected from the group consisting of unsubstituted, monosubstituted or disubstituted phenyl, phenoxy, benzyl, benzyloxy, naphthyl, and naphthoxy.

7. A compound according to claim 1, wherein $R_3$ and $R_4$ together with the nitrogen atom to which they are bound form a three- to ten-membered nitrogen heterocycle.

8. A compound according to claim 7, wherein said nitrogen heterocycle is selected from the group consisting of a morpholine group, a thiomorpholine group, a piperidine group, an azacycloheptane group, an azacyclooctane group, a 1,4-diaza-1-methylcycloheptane group, a piperazine group, a (N'—($C_1$–$C_6$-alkyl)piperazine group, a pyrrolidine group, an imidazolidine group, a pyrazolidine group, an aziridine group, a azetidine group, an indoline group, a carbazole group, a phenothiazine group, a phenazine group, a phenoxazine group, a tetrahydroquinoline group and a tetrahydroisoquinoline group.

9. A compound according to claim 1, wherein the —$NR_3R_4$ group in formula (I) represents diphenylamino, dianisylamino, morpholinyl, thiomorpholinyl, 3,5-dimethylthiomorpholinyl, piperidinyl, azacycloheptyl, azacyclooctyl, 1,4-diaza-1-methylcycloheptyl, piperazinyl, pyrrolidinyl, or 1,2,3,4-tetrahydroisoquinolinyl.

10. A compound according to claim 1, wherein at least one of B and B' is a phenyl group substituted in the para-position with an —$NR_3R_4$ group.

11. A photochromic article of manufacture comprising a synthetic resin body and a photochromic 3H-naphtho[2,1-b]pyran compound according to claim 1.

12. An article according to claim 11, wherein said synthetic resin body is an ophthalmic lens.

* * * * *